US008422017B2

(12) United States Patent
Gottwals et al.

(10) Patent No.: US 8,422,017 B2
(45) Date of Patent: Apr. 16, 2013

(54) COLOR ANALYSIS SYSTEM AND METHOD

(75) Inventors: Melanie M. Gottwals, San Jose, CA (US); Jeffrey M. DiCarlo, Menlo Park, CA (US); Nathan Moroney, Palo Alto, CA (US); Glen E. Montgomery, San Jose, CA (US); Steven W. Trovinger, Los Altos, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 517 days.

(21) Appl. No.: 12/536,643

(22) Filed: Aug. 6, 2009

(65) Prior Publication Data
US 2011/0032526 A1 Feb. 10, 2011

(51) Int. Cl.
*G01N 21/25* (2006.01)
(52) U.S. Cl.
USPC .............. 356/405; 356/402; 356/425; 356/71

(58) Field of Classification Search .................. 356/402, 356/405, 425, 445, 71, 620
See application file for complete search history.

(56) References Cited

U.S. PATENT DOCUMENTS

| 6,057,912 | A * | 5/2000 | Celentano et al. ............. 356/411 |
| 6,498,440 | B2 * | 12/2002 | Stam et al. ..................... 315/291 |
| 7,283,240 | B2 * | 10/2007 | Mestha et al. ................. 356/402 |
| 7,394,541 | B1 | 7/2008 | DiCarlo et al. |
| 7,466,416 | B2 | 12/2008 | Baker et al. |
| 2007/0046941 | A1 | 3/2007 | Mestha et al. |
| 2008/0174788 | A1 | 7/2008 | Ehbets et al. |

\* cited by examiner

*Primary Examiner* — Gregory J Toatley
*Assistant Examiner* — Iyabo S Alli

(57) ABSTRACT

A color analysis system includes a light source and a sensor configured to provide an output signal in response to reflected light received from the first light source. A controller receives the output signal and is configured to determine an adjustment factor based on the output signal, and determine a color based on the output signal and the adjustment factor.

17 Claims, 5 Drawing Sheets

FIG. 9

|  | tile 1 | . | . | . | . | . | . | tile 9 |  |
|---|---|---|---|---|---|---|---|---|---|
|  | 0.8748 | 0.0050 | 0.6194 | 0.2482 | 0.0471 | 0.1010 | 0.1221 | 0.4102 | 0.0592 | LED 1
|  | 0.8802 | 0.0051 | 0.6195 | 0.2469 | 0.0474 | 0.0847 | 0.1880 | 0.4165 | 0.0314 |
|  | 0.8869 | 0.0051 | 0.6220 | 0.2486 | 0.0496 | 0.0788 | 0.2725 | 0.2415 | 0.0154 | .
|  | 0.8871 | 0.0042 | 0.6198 | 0.2494 | 0.0496 | 0.1258 | 0.1594 | 0.1141 | 0.0149 | .
|  | 0.8899 | 0.0035 | 0.6200 | 0.2496 | 0.0470 | 0.2077 | 0.1180 | 0.0794 | 0.0118 | .
|  | 0.8900 | 0.0041 | 0.6188 | 0.2482 | 0.0499 | 0.3663 | 0.1085 | 0.0716 | 0.0125 |
|  | 0.8900 | 0.0043 | 0.6187 | 0.2482 | 0.0506 | 0.3682 | 0.1090 | 0.0722 | 0.0152 |
|  | 0.8797 | 0.0049 | 0.6196 | 0.2471 | 0.0468 | 0.0832 | 0.1816 | 0.4189 | 0.0314 | LED 8

FIG. 10

$$\begin{bmatrix} \text{diffuse} \\ \text{cal} \end{bmatrix} = \begin{bmatrix} 172.34 & 3.96 & 120.73 & 49.42 & 10.96 & 19.81 & 26.48 & 93.03 & 14.78 \\ 831.29 & 832.96 & 830.21 & 833.21 & 834.09 & 834.35 & 833.58 & 833.16 & 833.03 \end{bmatrix}$$

FIG. 11

$$\begin{bmatrix} \text{diffuse ambient} \\ \text{cal ambient} \end{bmatrix} = \begin{bmatrix} 0.01 & 0.00 & 0.00 & 0.00 & 0.00 & 0.01 & 0.00 & 0.00 & 0.00 \\ 0.29 & 0.27 & 0.32 & 0.19 & 0.32 & 0.28 & 0.18 & 0.26 & 0.24 \end{bmatrix}$$

$$[\text{desired reflect}] = [0.8748 \quad 0.0050 \quad 0.6194 \quad 0.2482 \quad 0.0471 \quad 0.1010 \quad 0.1221 \quad 0.4102 \quad 0.0592]$$

FIG. 12

$$[\text{desired reflect}] = \begin{bmatrix} A & C \\ B & D \end{bmatrix} \begin{bmatrix} \text{diffuse} - \text{ambient} \\ \text{cal} - \text{ambient} \end{bmatrix}$$

FIG. 13

$$\begin{bmatrix} A & C \\ B & D \end{bmatrix} = \begin{bmatrix} 3.7434 & -0.0014 \\ -0.5796 & 1.0000 \end{bmatrix}$$

FIG. 14

$$\begin{bmatrix} \text{diffuse} \\ \text{cal} \end{bmatrix} = \begin{bmatrix} 170.99 \\ 824.72 \end{bmatrix}$$

FIG. 15

$$\begin{bmatrix} \text{diffuse compensated} \\ \text{cal compensated} \end{bmatrix} = \begin{bmatrix} A & C \\ B & D \end{bmatrix} * \begin{bmatrix} \text{diffuse} \\ \text{cal} \end{bmatrix}$$

FIG. 16

$$\begin{bmatrix} \text{diffuse compensated} \\ \text{cal compensated} \end{bmatrix} = \begin{bmatrix} 3.7434 & -0.0014 \\ -0.5796 & 1.0000 \end{bmatrix} * \begin{bmatrix} 170.99 \\ 824.72 \end{bmatrix}$$

FIG. 17

$$\begin{bmatrix} \text{diffuse compensated} \\ \text{cal compensated} \end{bmatrix} = \begin{bmatrix} 3.7434*170.99 \; -0.0014*824.72 \\ -0.5796*170.99 + 1*824.72 \end{bmatrix} = \begin{bmatrix} 638.93 \\ 725.61 \end{bmatrix}$$

FIG. 18

COLOR ANALYSIS SYSTEM AND METHOD

CROSS-REFERENCE TO RELATED APPLICATION

This application is related to commonly assigned U.S. patent application Ser. No. 12/436,240, filed on May 6, 2009, which is incorporated by reference.

BACKGROUND

The colors produced by color printers can vary as a function of media type, ink, print heads, temperature, humidity, etc. Color management products allow the creation of device characterization profiles for devices such as printers. These profiles, such as International Color Consortium (ICC) compliant profiles, allow for proper color handling across many types of devices. For example, in order to create a printer profile, the printer outputs a test sheet of color patches arranged in a predetermined pattern. A color measurement device such as a spectrophotometer or calorimeter then scans the color patches, and the color measurements can be used create a profile for the printer that can be used to insure uniform color display.

Some hand held spectrophotometers include a contact device such as a wheel that contacts the color patches on the paper. This maintains a desired spatial relationship between the spectrophotometer and the paper, and as the spectrophotometer is moved, the wheel measures the speed and direction of the movement. Because the spectrophotometer device contacts the paper, it can distort the color patches, making the measurement by the spectrophotometer inaccurate.

In other known systems, a color measurement device such as a spectrophotometer or calorimeter is mounted in the paper path of the moving sheets in a printer to provide color measurements of the test color patches printed on the sheets as they pass the color measurement device. With a system such as this, the color measurement device does not contact the paper. However, such non-contact color measurement systems can be sensitive to variation in the distance between the color measurement device and the test color patches. Factors such as differences in media thickness or variations in a paper's position as it travels through a printer thus can reduce accuracy of the color measurement.

For these and other reasons, a need exists for the present invention.

BRIEF DESCRIPTION OF THE DRAWINGS

FIG. 9 illustrates example desired reflectance values.

FIGS. 10-14 illustrate example calculations for determining adjustment factors.

FIGS. 15-18 illustrate example calculations for applying the adjustment factors to color measurements.

DETAILED DESCRIPTION

In the following detailed description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

In the following disclosure, specific details may be set forth in order to provide a thorough understanding of the disclosed systems and methods. It should be understood however, that all of these specific details may not be required in every implementation. In other instances, well-known methods, procedures, components, circuits, and networks have not been described in detail so as not to unnecessarily obscure the disclosed systems and methods.

It will also be understood that, although the terms first, second, etc. are used herein to describe various elements, these elements should not be limited by these terms. These terms are only used to distinguish one element from another.

Figure 1:
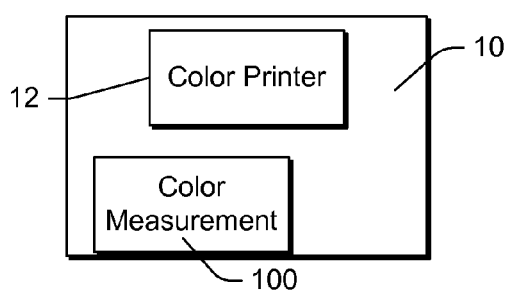
FIG. 1 is a block diagram conceptually illustrating an embodiment of a printer system.

FIG. 1 conceptually illustrates portions of an embodiment of a printer system 10, which includes a color printer 12, such as a color laser or ink printer. It is desirable for a color printer system to measure the colors of test patches on a printed test sheet. This allows for real-time, automatic printer color correction. Thus the printer system 10 includes a color analysis system 100. In the illustrated embodiments, the color analysis system 100 is configured as a non-contact system. In other words, the system 100 does not contact printed sheets produced by the printer 12.

Figure 2:
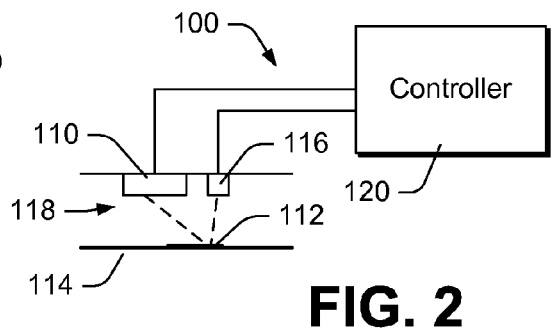
FIG. 2 is a block diagram conceptually illustrating an embodiment of a color analysis system.

FIG. 2 broadly illustrates aspects of an embodiment of the color analysis system 100. The system 100 includes a light source 110 that is configured to illuminate a test patch 112 on a test sheet 114. In some embodiments, a plurality of light sources are provided providing light of various colors. A sensor 116 is configured to receive light 118 from the light source 110 reflected from the test patch 112 and provide an output signal based on the received light. A controller 120 receives the output signal from the sensor 116 and is configured to determine the color of the test patch 112 based on the output signal.

Embodiments of the controller 120 may be implemented by one or more discrete modules (or data processing components) that are not limited to any particular hardware, firmware, or software configuration. In some embodiments, the controller 120 is a component of the printer 10, and in other embodiments, the color analysis system itself includes a dedicated controller 120. The controller 120 may be implemented in any computing or data processing environment, including in digital electronic circuitry (e.g., an application-specific integrated circuit, such as a digital signal processor (DSP)) or in computer hardware, firmware, device driver, or software. In some embodiments, the functionalities of the modules are combined into a single data processing component. In some embodiments, the respective functionalities of each of one or more of the modules are performed by a respective set of multiple data processing components.

In some implementations, process instructions (e.g., machine-readable code, such as computer software) for implementing the methods that are executed by the embodiments of the controller 120, as well as the data it generates, are stored in one or more machine-readable media. Storage devices suitable for tangibly embodying these instructions and data include all forms of computer-readable memory, including, for example, semiconductor memory devices, such as EPROM, EEPROM, and flash memory devices, magnetic disks such as internal hard disks and removable hard disks, magneto-optical disks, DVD-ROM/RAM, and CD-ROM/RAM.

Figure 3:
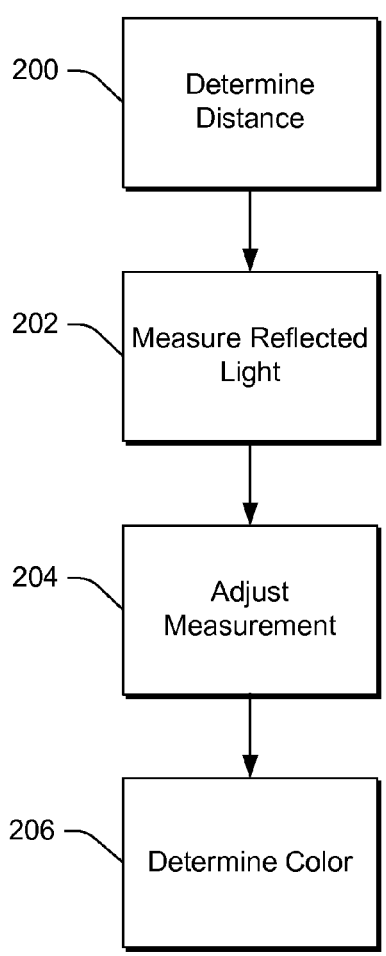
FIG. 3 is a flow diagram illustrating an embodiment of a color analysis method.

FIG. 3 broadly illustrates a color analysis method implemented by the color analysis system 100. As noted above, in some embodiments the system 100 is a non-contact system wherein the color measurement device does not contact the paper. As such, the measurement system can be sensitive to variation in the distance between the color measurement device and the test color patches. In block 200, the system determines the distance between the light source 110 and the test patch 112. In block 202, light reflected by the test patch is measured, and in block 204 the measured light is adjusted based on the determined distance from block 200. The color of the test patch is determined based on the adjusted measured light in block 206.

Figure 4:
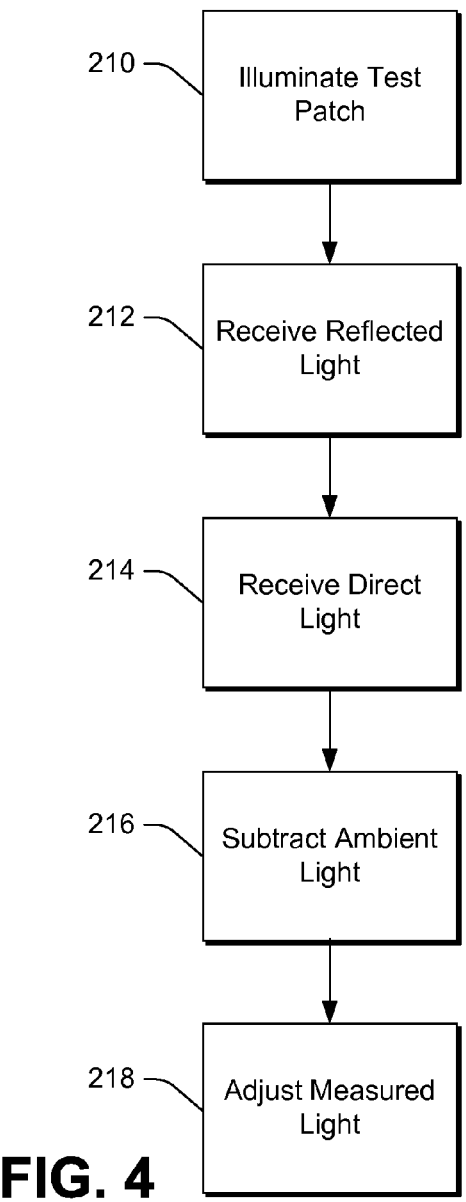
FIG. 4 is a flow diagram illustrating an embodiment of a color analysis method.

FIG. 4 illustrates further aspects of the color analysis process in accordance with some embodiments. In block 210, the test patch 112 is illuminated using the light source 110, and light reflected by the test patch 112 is received and measured by the sensor 116 in block 212. As noted above, the sensor 116 provides an output signal to the controller 120 representing the measured light.

Figure 5:
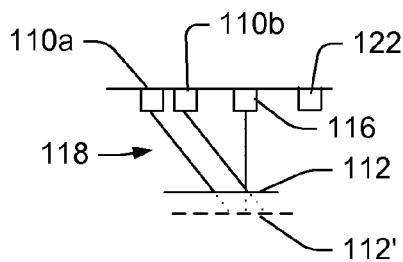
FIG. 5 is a block diagram conceptually illustrating aspects of an embodiment of a color analysis system.

In some embodiments, such as the embodiment illustrated in FIG. 5, a second sensor 122 is provided that is configured to receive light directly from the light source 110. The second sensor 122 measures changes in intensity of the light source 110, which among other things allows adjusting the system in response to any light source intensity shift over time.

Referring back to FIG. 4, light received directly from the light source 110 is received and measured by the second sensor 122 in block 214, and a corresponding output signal is provided to the controller 120. In block 216, ambient light is subtracted from the light measured in blocks 212 and 214. The light measurements are adjusted in block 218 based on the distance between the light source 110 and the sensor 116.

In the embodiment illustrated in FIG. 5, the light source 110 includes two LEDs 110a and 110b that are spaced apart from each other. This spacing causes the light to reflect off of the test patch 112 at slightly different angles. As the distance between the LEDs 110a, 110b and the test patch 112 varies; for example, between the test patches 112 and 112', these angle differences causes the light pattern from each LED 110a, 110b to shift differently.

Figure 6:
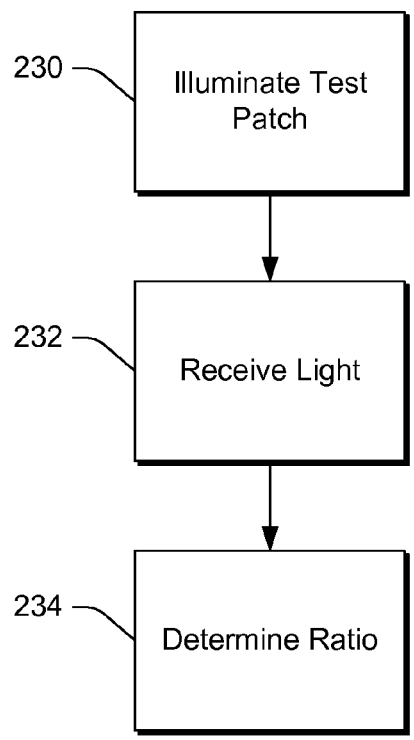
FIG. 6 is a flow diagram illustrating aspects of an embodiment of a color analysis method.

FIG. 6 illustrates aspects of a process for determining the distance between the light source 110 and the test patch 110 implemented in some embodiments. The light sources 110a, 110b are used to illuminate the test patch 112 in block 230. In some embodiments, the sensors 116 and 122 are photo sensors that receive light and output a diffuse signals. The LEDs 110a, 110b emit light having the same color, which in certain embodiments is red light having a nominal peak wavelength of 650 nm.

Reflected light is received by the sensor 116 (and if applicable, the sensor 122 directly receives light) in Block 232. By measuring the intensity of the reflected light from each LED 110a, 110b sequentially using the sensor 116 and taking the ratio of the result, the distance between the sensor 116 and the test patch can be determined in Block 234.

Figure 7A:
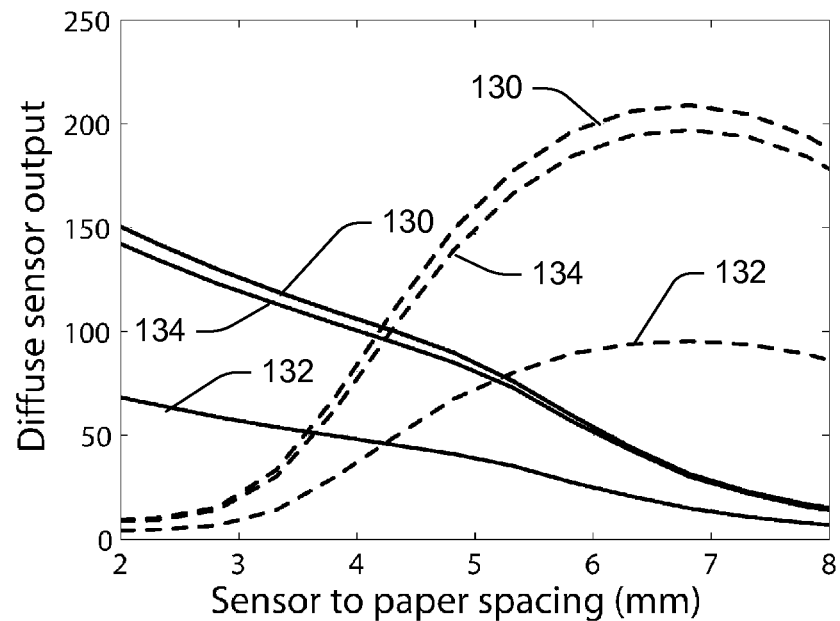
FIG. 7A illustrates intensity measurements as a function of height for different colored test patches.
Figure 7B:
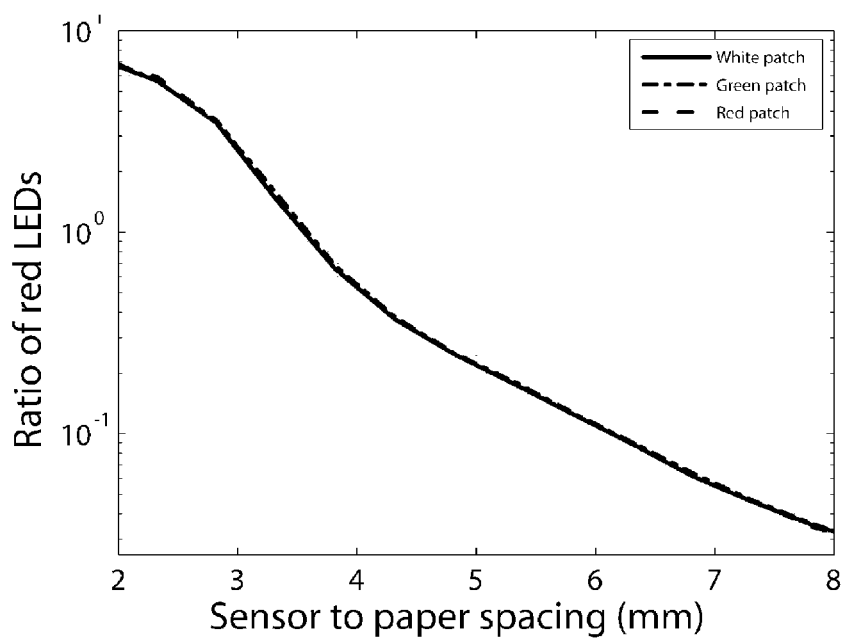
FIG. 7B illustrates ratios of the measurements illustrated in FIG. 6A.

FIG. 7A illustrates intensity measurements from two red LEDs as a function of height for different colored test patches, including white 130, green 132 and red 134 test patches. In FIG. 7A, the solid lines represent the sensor output for the first LED 110a and the broken lines represent the sensor output for the second LED 110b for each of the different colored test patches 130, 132 and 134. FIG. 7B illustrates the resulting ratios of the two measurements for the same test patches. The ratio plot of FIG. 7B shows a direct correlation between the ratio of the output signals of the sensor 116 for the two light sources and the module height. Moreover, because the LEDs are the same color, this ratio does not change for different colored patches or media types (assuming enough light is reflected from the patch). Thus, in accordance with certain embodiments, the color adjustment is based on the ratio of reflected light received from the first LED to reflected light received from the second LED.

In some embodiments, a second set of light sources are provided for use in determining the color adjustment, including third and fourth LEDs. The first and second LEDs emit light of a first color, and the second and third LEDs emit light of a second color. In an exemplary embodiment, the first and second LEDs emit red light, and the third and fourth LEDs emit cyan light. Both sets of LEDs are used to illuminate the test patch, and the output signals from one of the sets of LEDs is used to determine the color adjustment.

Embodiments of the color analysis system 100 operate as a calorimeter. More specifically, the system 100 can reproduce color measurements (XYZ values, LAB values or spectral reflectance functions) that are valid for a set of predefined illuminants and any ink/media combination. (Measurements from a spectrophotometer are valid for any arbitrary illuminant.) In the illustrated embodiment, the light source 110 includes five LEDs in addition to the red (650 nm) LEDs used for the distance determination. One of the LEDs 110a, 110b is used for both the color adjustment determination and color measurement, so six LEDs in total are used for the color determination. In other embodiments, there are a total of eight LEDs, where two red LEDs and two cyan LEDs are used for the color adjustment determination, and one of the red and one of the cyan LEDs are used with the remaining four LEDs for the color determination.

The LEDs used for the color determination emit light at different peak wavelengths across the visible spectrum. In some embodiments, LEDs emitting light having nominal peak wavelengths of 450 nm, 470 nm, 520 nm, 560 nm, 610 nm and 650 nm are used for color sensing.

Thus, referring back to FIG. 4, in block 210 the test patch 112 is illuminated in sequence using each of the six LEDs. The reflected light is received by the sensor 116 (and directly by the second sensor 122 where applicable) in blocks 212 and 214. In some implementations, the desired LED and both sensors 116, 122 are turned on. The signal received by the sensors is integrated, then the LED and sensors are turned off. This sequence is repeated for each LED.

As noted herein, color measurement accuracy can vary if the position of the system 100 is moved away from its nominal height position relative to the test patch 112. Thus, to maintain the color measurement accuracy over varying heights, the light measurements are adjusted in block 218.

In some embodiments, an adjustment factor is applied to the sensor's 116 output signal. The adjustment factor is determined based on the distance between the sensor 116 and the test patch 112. As noted above, this can include determining the ratio of the reflected light received from the first LED 110a to the reflected light received from the second LED 110b. This ratio provides an indication of the distance between the light sources 110 and the color patch 112, and can thus further be used to calculate this distance.

As noted above, the controller 120 includes or has access to a memory. In some embodiments, the memory stores adjustment factors corresponding to various distances between the light source 110 and the test patch 112, for example. In such embodiments, the controller 120 is configured to select an adjustment factor based the determined distance between the light source 110 and the test patch 112, and apply the selected adjustment factor to the output signal provided by the sensor 116.

Figure 8:
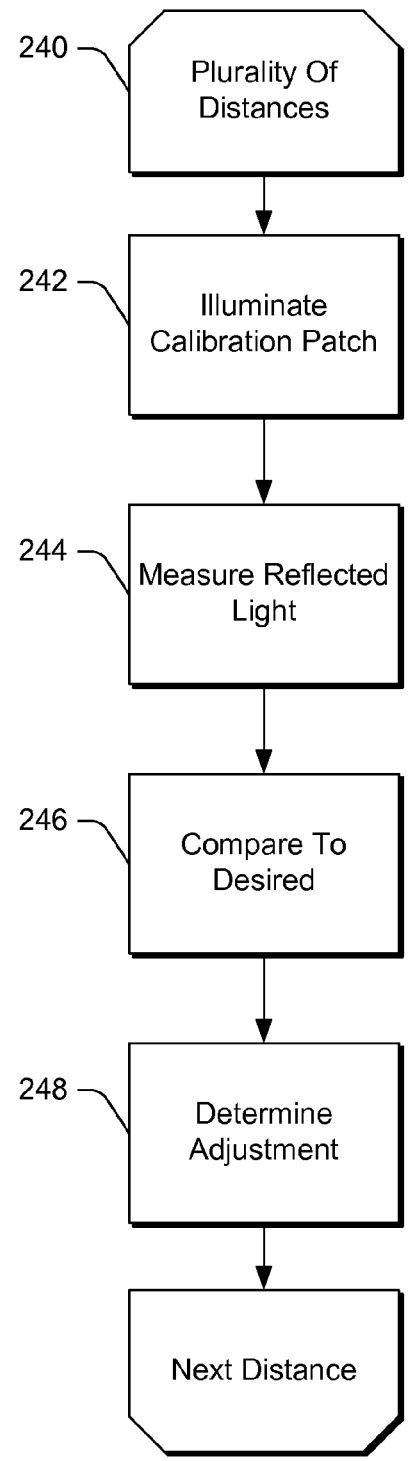
FIG. 8 is a flow diagram illustrating of an embodiment of a color analysis method.

FIG. 8 generally illustrates a process for determining the adjustment factors in accordance with certain embodiments. As shown in block 240, a light source such as the light source 110 is positioned at various known distances from a color calibration patch having a known color. At each of the distances, the calibration patch is illuminated in block 242. The light reflected by the color calibration patch is measured at each of the distances in block 244, and the measured light is compared to a desired reflected light value for the corresponding color in block 246. The adjustment factor for the respective distance is determined based on the measured reflected light compared to the desired value in block 248. In some embodiments, several calibration patches are used having different known colors.

In a particular embodiment, the color calibration patches are nine BCRA Glossy Ceramic Color tiles. Yellow, orange and red tiles were eliminated due to translucency issues. Readings were taken for both the first and second sensors 116, 122, measuring the received reflected and direct light from the light sources 110, at the center of each tile. Ambient light was also measured at each tile and later removed from the reflected and direct light measurements. The measurements were repeated at multiple distances between the light source and the tile. A laser displacement sensor, for example, can be used to measure and adjust the distances. In an example embodiment, measurements are taken at 0.1 mm increments over a +/−1.5 mm range. As noted above, the light sources in some embodiments are LEDs, for example, eight LEDs providing light of six different colors (two sets of same-colored LEDs are also used for the height determination). With such arrangements, the measurements are repeated for each of the LEDs. Different conditioning gain factors can be computed for each LED and for each calibration distance or height.

In one embodiment, the adjustment factors are determined by the following model:

desired reflectance=$(A*Mdiff+C*Mcal)/(B*Mdiff+D*Mcal)$

The desired reflectance is determined using use certified BCRA tile reflectance measurements made by Ceram Technology and LED spectral responses measured, for example, using a calorimeter.

The first sensor 116, which receives light reflected from the tiles, is referred to as the "diffuse sensor," and the second sensor 122, which receives light directly from the LEDs 110 is referred to as the "calibration sensor." Thus, Mdiff and Mcal refer to the raw diffuse and calibration sensor digital measurement counts, respectively. A,B,C and D are four model gain factors. In some implementations, ambient light is subtracted from the diffuse and calibration sensor counts before calculation of the gain factors.

The gain factor D is set to 1, and the remaining gains A, B, and C are solved for each LED, using all nine BCRA tile diffuse and calibration sensor measurements to compute model gains. In alternative embodiments, fewer tiles are used, such as only white, black and one other colored tile.

Example desired reflectance values for the nine color tiles and eight LEDs are shown in FIG. 9. An example of solving for gains A,B,C and D using the desired reflectance values for LED 1 is illustrated in FIGS. 10-14. Example raw measurements from the diffuse and calibration sensors for LED 1 are shown in FIG. 10, and the corresponding ambient light measurements for the diffuse and calibration sensors are shown in FIG. 11. The desired reflectance values from FIG. 9 for LED 1 are illustrated in FIG. 12.

As noted above, the gains are determined by desired reflectance=$(A*Mdiff+C*Mcal)/(B*Mdiff+D*Mcal)$ which is restated in FIG. 13. Gain D is set to 1, and the remaining gains A,B and C are solved as illustrated in FIG. 14, resulting in adjustment factors of 3.7434, −0.5796, −0.0014 and 1.000 for gains A,B,C and D, respectively. The process is repeated for each LED in the system and at each of the predetermined distances between the light source and the color tile, and the gain values are stored for access by the controller 120.

The appropriate saved gain factors are determined based on the distance between the light source 110 and the test patch 112, and applied to the output signal from the sensors 116, 122 (where applicable). FIGS. 15-18 illustrate an example of this process, applying the gain factors determined in the example of FIGS. 9-14.

Example measurements from the diffuse and calibration sensors 116, 122 for one of the light sources, or LEDs 110 are shown in FIG. 15. In some embodiments, the sensors 116, 122 further measure the ambient light which is subtracted from the raw diffuse and calibration sensor measurements. The light measurements are adjusted as shown in FIG. 16, applying the gain factors to the output signals from the sensors 116, 122. The distance between the light source 110 and test patch 112 is determined, and assuming that the gain factors of FIG. 14 correspond to the determined distance, the gain factors are applied as illustrated in FIGS. 16-18. The adjusted diffuse sensor measurement is then divided by the adjusted calibration sensor measurement as follows:

638.93/725.61=0.881 resulting in an adjusted reflectance value of 0.881. This process is repeated for each of the LEDs.

The calculated reflectance values are then transformed into LAB values for a specific illuminant using a color correction matrix (CCM). The reflectance values for each of the LEDs are applied to the CCM, resulting in XYZ values, which are then converted to Lab values. In some embodiments, different CCM values are computed for the predetermined distances between the light source and the test patch, and in other embodiments, a single CCM computed at a nominal distance is used for all distances.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A color analysis system, comprising:
   a first light source configured to illuminate a test patch;
   a first sensor configured to provide a first output signal in response to light received from the first light source reflected by the test patch;
   a second sensor configured to provide a second output signal in response to light received directly from the first light source;
   a controller receiving the first and second output signals and configured to determine an adjustment factor based on the first and second output signals, and determine a color based on the first and second output signals and the adjustment factor.

2. The color analysis system of claim 1, wherein:
   the controller is configured to determine a distance between the first light source and the test patch based on the first output signal.

3. The color analysis system of claim 2, further comprising:
   a second light source spaced apart from the first light source, wherein the first and second light sources emit light of the same color;
   wherein the first sensor is configured to receive light reflected by the test patch from the first and second light sources; and
   wherein the controller is configured to determine the distance between the first light source and the test patch based on the reflected light received by the first sensor from the first and second light sources.

4. The color analysis system of claim 2, further comprising:
   a memory accessible by the controller, the memory storing a plurality of adjustment factors corresponding to a plurality of distances between the first light source and the test patch;
   wherein the controller is configured to select an adjustment factor in response to the determined distance, and apply the selected adjustment factor to the output signal.

5. The color analysis system of claim 4, wherein the plurality of adjustment factors stored in the memory are determined by a method comprising:
   positioning a light source at a plurality of distances from a color calibration patch having a known color;
   illuminating the color calibration patch at each of the distances;
   measuring light reflected by the color calibration patch at each of the distances;
   comparing the measured reflected light for each of the distances to a desired reflected light value; and
   determining an adjustment factor for each of the distances based on the comparisons.

6. The color analysis system of claim 5, wherein the method for determining the plurality of adjustment factors stored in the memory further comprises:
   positioning the light source at a plurality of distances from a plurality of color calibration patches having known colors;
   illuminating each of the color calibration patches at each of the distances;
   measuring light reflected by the color calibration patches at each of the distances;
   comparing the measured reflected light for the color calibration patches at each of the distances to a desired reflected light value; and
   determining an adjustment factor for each of the distances based on the comparisons.

7. A color analysis method, comprising:
   determining a distance between a light source and a test patch, including illuminating the test patch with first and second spaced apart light sources emitting light of the same color, and calculating a ratio of an intensity of the light received from the first light source to an intensity of the light received from the second light source;
   measuring light reflected by the test patch;
   adjusting the measured light based on the determined distance;
   determining a color of the test patch based on the adjusted measured light.

8. The color analysis method of claim 7, further comprising:
   illuminating the test patch with a light source;
   measuring light reflected by the test patch received by a first sensor;
   measuring light received directly from the light source by a second sensor; and
   adjusting the measured reflected light and the measured direct light.

9. The color analysis method of claim 7, further comprising:
   subtracting ambient light from the measured light.

10. The color analysis method of claim 7, further comprising:
    illuminating the test patch with a plurality of light sources;
    measuring light reflected by the test patch for each of the light sources; and
    adjusting the measured reflected light and the measured direct light.

11. The color analysis method of claim 10, further comprising:
    receiving light from each of the light sources by a first sensor.

12. The color analysis method of claim 7, further comprising:
    receiving light reflected by the test patch from the first and second light sources by a first sensor.

13. The color analysis method of claim 7, further comprising:
    determining a plurality of adjustment factors corresponding to a plurality of distances;
    selecting an adjustment factor in response to the determined distance; and
    applying the selected adjustment factor to the measured light.

14. The color analysis method of claim 13, wherein determining the plurality of adjustment factors includes:
    positioning a light source at a plurality of distances from a color calibration patch having a known color;
    illuminating the color calibration patch at each of the distances;
    measuring light reflected by the color calibration patch at each of the distances;
    comparing the measured reflected light for each of the distances to a desired reflected light value; and
    determining an adjustment factor for each of the distances based on the comparisons.

15. The color analysis method of claim 14, further comprising:
    positioning the light source at a plurality of distances from a plurality of color calibration patches having known colors;

illuminating each of the color calibration patches at each of the distances;
measuring light reflected by the color calibration patches at each of the distances;
comparing the measured reflected light for the color calibration patches at each of the distances to a desired reflected light value; and
determining an adjustment factor for each of the distances based on the comparisons.

16. A color analysis method, comprising:
positioning a first light source at a plurality of distances from a color calibration patch having a known color;
illuminating the color calibration patch at each of the distances;
measuring light reflected by the color calibration patch at each of the distances;
comparing the measured reflected light for each of the distances to a desired reflected light value;
determining an adjustment factor for each of the distances based on the comparisons;
determining a distance between the light source and a test patch;
illuminating the test patch with a second light source;
measuring light from the second light source reflected by the test patch;
measuring light received directly from the second light source;
selecting an adjustment factor in response to the determined distance;
applying the selected adjustment factor to the measured light; and
determining a color of the test patch based on the adjusted measured light.

17. The color analysis method of claim 16, further comprising:
positioning the light source at a plurality of distances from a plurality of color calibration patches having known colors;
illuminating each of the color calibration patches at each of the distances;
measuring light reflected by the color calibration patches at each of the distances;
comparing the measured reflected light for the color calibration patches at each of the distances to a desired reflected light value; and
determining an adjustment factor for each of the distances based on the comparisons.

* * * * *